(12) United States Patent
Wang et al.

(10) Patent No.: US 11,912,988 B2
(45) Date of Patent: Feb. 27, 2024

(54) METHOD AND KIT FOR CONSTRUCTING A SIMPLIFIED GENOMIC LIBRARY

(71) Applicant: China National Rice Research Institute, Zhejiang (CN)

(72) Inventors: Kejian Wang, Zhejiang (CN); Qing Liu, Zhejiang (CN)

(73) Assignee: China National Rice Research Institute, Zhejiang (CN)

( * ) Notice: Subject to any disclaimer, the term of this patent is extended or adjusted under 35 U.S.C. 154(b) by 75 days.

(21) Appl. No.: 16/471,584

(22) PCT Filed: Jan. 26, 2018

(86) PCT No.: PCT/CN2018/074329
§ 371 (c)(1),
(2) Date: Jun. 20, 2019

(87) PCT Pub. No.: WO2018/113799
PCT Pub. Date: Jun. 28, 2018

(65) Prior Publication Data
US 2020/0224192 A1 Jul. 16, 2020

(30) Foreign Application Priority Data
Dec. 21, 2016 (CN) .......................... 201611193343.X (51) Int. Cl.
*C12N 15/10* (2006.01)
*C40B 50/06* (2006.01)

(52) U.S. Cl.
CPC .......... *C12N 15/1093* (2013.01); *C40B 50/06* (2013.01)

(58) Field of Classification Search
CPC .......................... C12N 15/1093; C40B 50/06
See application file for complete search history.

(56) References Cited

U.S. PATENT DOCUMENTS

| 10,036,013 B2 * | 7/2018 | Kim .................. C12N 15/1086 |
| 10,087,485 B2 * | 10/2018 | Muir et al. ........... C12Q 1/6876 |
| 2019/0233889 A1 * | 8/2019 | Enoki et al. ......... C12Q 1/6874 |

FOREIGN PATENT DOCUMENTS

| CN | 102656279 A | 9/2012 |
| CN | 103397089 A | 11/2013 |
| CN | 104561294 A | 4/2015 |
| CN | 105696088 A | 6/2016 |
| CN | 105985945 A | 10/2016 |
| CN | 106676099 A | 5/2017 |
| JP | 2016-178528 | * 9/2016 |

OTHER PUBLICATIONS

Froussard "rPCR: A Powerful Tool for Random Amplification of Whole RNA Sequences" Genome Res. 1993 2: 185-190 (Year: 1993).*

(Continued)

*Primary Examiner* — Jeremy C Flinders
(74) *Attorney, Agent, or Firm* — Gang Yu (57) ABSTRACT

Provided are a method and a kit for constructing a simplified genomic library. The method comprises: performing a non-specific amplification on a whole genome with a first pair of primers to obtain random amplified fragments; performing a specific amplification on the random amplified fragments with a second pair of primers to obtain the simplified genomic library.

2 Claims, 3 Drawing Sheets

Specification includes a Sequence Listing.

(56) References Cited

OTHER PUBLICATIONS

Grothues et al. "PCR amplification of megabase DNA with tagged random primers (T-PCR)" Nucleic Acids Res. 1993, 21(5): 1321-1322 (Year: 1993).*
Wei, Shujun, et al. RAD-seq and its application in entomological research. Acta Entomologica Sinica. Sep. 21, 2016 (Sep. 21, 2016). vol. 59 No. 7. pp. 767-774, only abstract translated.
Michael A. Russello et al. Frompromise to practice: pairing non-invasive sampling with genomics in conservation. Peer J. Jul. 21, 2015 (Jul. 21, 2015). vol. 3. pp. 1-18.

* cited by examiner performing a non-specific amplification on a whole genome with a first pair of primers to obtain random amplified fragments;

↓ performing a specific amplification on the random amplified fragments with a second pair of primers to obtain the simplified genomic library

SEQUENCE LISTING

```
<160> NUMBER OF SEQ ID NOS: 32

<210> SEQ ID NO 1

<400> SEQUENCE: 1

000

<210> SEQ ID NO 2

<400> SEQUENCE: 2

000

<210> SEQ ID NO 3
<211> LENGTH: 36
<212> TYPE: DNA
<213> ORGANISM: Artificial Sequence
<220> FEATURE:
<223> OTHER INFORMATION: 1-1F

<400> SEQUENCE: 3
gacgctcttc cgatctcagt aggttctgga ctaacg                              36

<210> SEQ ID NO 4
<211> LENGTH: 36
<212> TYPE: DNA
<213> ORGANISM: Artificial Sequence
<220> FEATURE:
<223> OTHER INFORMATION: 1-2F
```

```
<400> SEQUENCE: 4
gacgctcttc cgatctcagt aggttctgga ctaaca                             36

<210> SEQ ID NO 5
<211> LENGTH: 36
<212> TYPE: DNA
<213> ORGANISM: Artificial Sequence
<220> FEATURE:
<223> OTHER INFORMATION: 1-3F

<400> SEQUENCE: 5
gacgctcttc cgatctcagt aggttctgga ctaact                             36

<210> SEQ ID NO 6
<211> LENGTH: 36
<212> TYPE: DNA
<213> ORGANISM: Artificial Sequence
<220> FEATURE:
<223> OTHER INFORMATION: 1-4F

<400> SEQUENCE: 6
gacgctcttc cgatctcagt aggttctgga ctaagg                             36

<210> SEQ ID NO 7
<211> LENGTH: 32
<212> TYPE: DNA
<213> ORGANISM: Artificial Sequence
<220> FEATURE:
<223> OTHER INFORMATION: 1-1R

<400> SEQUENCE: 7
gacgtgtgct cttccgatct tctggactat gc                                 32

<210> SEQ ID NO 8
<211> LENGTH: 32
<212> TYPE: DNA
<213> ORGANISM: Artificial Sequence
<220> FEATURE:
<223> OTHER INFORMATION: 1-2R

<400> SEQUENCE: 8
gacgtgtgct cttccgatct tctggactat gg                                 32

<210> SEQ ID NO 9
<211> LENGTH: 32
<212> TYPE: DNA
<213> ORGANISM: Artificial Sequence
<220> FEATURE:
<223> OTHER INFORMATION: 1-3R

<400> SEQUENCE: 9
gacgtgtgct cttccgatct tctggactat ga                                 32

<210> SEQ ID NO 10
<211> LENGTH: 32
<212> TYPE: DNA
<213> ORGANISM: Artificial Sequence
<220> FEATURE:
<223> OTHER INFORMATION: 1-4R

<400> SEQUENCE: 10
gacgtgtgct cttccgatct tctggactat gt                                 32

<210> SEQ ID NO 11
<211> LENGTH: 62
```

```
<212> TYPE: DNA
<213> ORGANISM: Artificial Sequence
<220> FEATURE:
<223> OTHER INFORMATION: upstream primer of the 2nd round of PCR

<400> SEQUENCE: 11
aatgatacgg cgaccaccga gatctacact ctttccctac acgacgctct tccgatctca     60
gt                                                                    62

<210> SEQ ID NO 12
<211> LENGTH: 70
<212> TYPE: DNA
<213> ORGANISM: Artificial Sequence
<220> FEATURE:
<223> OTHER INFORMATION: dowmstream primer of the 2nd round of PCR

<400> SEQUENCE: 12
caagcagaag acggcatacg agatcgctga tcgtgactgg agttcagacg tgtgctcttc     60
cgatctcagt                                                            70

<210> SEQ ID NO 13
<211> LENGTH: 39
<212> TYPE: DNA
<213> ORGANISM: Artificial Sequence
<220> FEATURE:
<223> OTHER INFORMATION: 2-1F

<400> SEQUENCE: 13
cgacgctctt ccgatcttga cgccatgtct ggactaaca                            39

<210> SEQ ID NO 14
<211> LENGTH: 39
<212> TYPE: DNA
<213> ORGANISM: Artificial Sequence
<220> FEATURE:
<223> OTHER INFORMATION: 2-2F

<400> SEQUENCE: 14
cgacgctctt ccgatcttga cgccacatct ggactaaca                            39

<210> SEQ ID NO 15
<211> LENGTH: 39
<212> TYPE: DNA
<213> ORGANISM: Artificial Sequence
<220> FEATURE:
<223> OTHER INFORMATION: 2-3F

<400> SEQUENCE: 15
cgacgctctt ccgatcttga cgccacttct ggactaaca                            39

<210> SEQ ID NO 16
<211> LENGTH: 39
<212> TYPE: DNA
<213> ORGANISM: Artificial Sequence
<220> FEATURE:
<223> OTHER INFORMATION: 2-4F

<400> SEQUENCE: 16
cgacgctctt ccgatcttga cgccacctct ggactaaca                            39

<210> SEQ ID NO 17
<211> LENGTH: 39
<212> TYPE: DNA
<213> ORGANISM: Artificial Sequence
<220> FEATURE:
```

<223> OTHER INFORMATION: 2-5F

<400> SEQUENCE: 17
cgacgctctt ccgatcttga cgccaggtct ggactaaca                          39

<210> SEQ ID NO 18
<211> LENGTH: 39
<212> TYPE: DNA
<213> ORGANISM: Artificial Sequence
<220> FEATURE:
<223> OTHER INFORMATION: 2-1R

<400> SEQUENCE: 18
gtgtgctctt ccgatctcag tcccatctct ggactatgg                          39

<210> SEQ ID NO 19
<211> LENGTH: 39
<212> TYPE: DNA
<213> ORGANISM: Artificial Sequence
<220> FEATURE:
<223> OTHER INFORMATION: 2-2R

<400> SEQUENCE: 19
gtgtgctctt ccgatctcag tcccatgtct ggactatgg                          39

<210> SEQ ID NO 20
<211> LENGTH: 39
<212> TYPE: DNA
<213> ORGANISM: Artificial Sequence
<220> FEATURE:
<223> OTHER INFORMATION: 2-3R

<400> SEQUENCE: 20
gtgtgctctt ccgatctcag tcccacatct ggactatgg                          39

<210> SEQ ID NO 21
<211> LENGTH: 39
<212> TYPE: DNA
<213> ORGANISM: Artificial Sequence
<220> FEATURE:
<223> OTHER INFORMATION: 2-4R

<400> SEQUENCE: 21
gtgtgctctt ccgatctcag tcccacttct ggactatgg                          39

<210> SEQ ID NO 22
<211> LENGTH: 39
<212> TYPE: DNA
<213> ORGANISM: Artificial Sequence
<220> FEATURE:
<223> OTHER INFORMATION: 2-5R

<400> SEQUENCE: 22
gtgtgctctt ccgatctcag tcccacctct ggactatgg                          39

<210> SEQ ID NO 23

<400> SEQUENCE: 23

000

<210> SEQ ID NO 24

<400> SEQUENCE: 24

000

<210> SEQ ID NO 25
<211> LENGTH: 78
<212> TYPE: DNA
<213> ORGANISM: Artificial Sequence
<220> FEATURE:
<223> OTHER INFORMATION: 3F-1

<400> SEQUENCE: 25
aatgatacgg cgaccaccga gatctacact ctttccctac acgacgctct tccgatctca    60
gtaggttctg gactaacg                                                  78

<210> SEQ ID NO 26
<211> LENGTH: 78
<212> TYPE: DNA
<213> ORGANISM: Artificial Sequence
<220> FEATURE:
<223> OTHER INFORMATION: 3-2F

<400> SEQUENCE: 26
aatgatacgg cgaccaccga gatctacact ctttccctac acgacgctct tccgatctca    60
gtaggttctg gactaaca                                                  78

<210> SEQ ID NO 27
<211> LENGTH: 78
<212> TYPE: DNA
<213> ORGANISM: Artificial Sequence
<220> FEATURE:
<223> OTHER INFORMATION: 3-3F

<400> SEQUENCE: 27
aatgatacgg cgaccaccga gatctacact ctttccctac acgacgctct tccgatctca    60
gtaggttctg gactaact                                                  78

<210> SEQ ID NO 28
<211> LENGTH: 78
<212> TYPE: DNA
<213> ORGANISM: Artificial Sequence
<220> FEATURE:
<223> OTHER INFORMATION: 3-4F

<400> SEQUENCE: 28
aatgatacgg cgaccaccga gatctacact ctttccctac acgacgctct tccgatctca    60
gtaggttctg gactaagg                                                  78

<210> SEQ ID NO 29
<211> LENGTH: 78
<212> TYPE: DNA
<213> ORGANISM: Artificial Sequence
<220> FEATURE:
<223> OTHER INFORMATION: 3-1R

<400> SEQUENCE: 29
caagcagaag acggcatacg agatcgctga tcgtgactgg agttcagacg tgtgctcttc    60
cgatcttctg gactatgc                                                  78

<210> SEQ ID NO 30
<211> LENGTH: 78
<212> TYPE: DNA
<213> ORGANISM: Artificial Sequence
<220> FEATURE:
<223> OTHER INFORMATION: 3-2R

```
<400> SEQUENCE: 30
caagcagaag acggcatacg agatcgctga tcgtgactgg agttcagacg tgtgctcttc        60
cgatcttctg gactatgg                                                      78

<210> SEQ ID NO 31
<211> LENGTH: 78
<212> TYPE: DNA
<213> ORGANISM: Artificial Sequence
<220> FEATURE:
<223> OTHER INFORMATION: 3-3R

<400> SEQUENCE: 31
caagcagaag acggcatacg agatcgctga tcgtgactgg agttcagacg tgtgctcttc        60
cgatcttctg gactatga                                                      78

<210> SEQ ID NO 32
<211> LENGTH: 78
<212> TYPE: DNA
<213> ORGANISM: Artificial Sequence
<220> FEATURE:
<223> OTHER INFORMATION: 3-4R

<400> SEQUENCE: 32
caagcagaag acggcatacg agatcgctga tcgtgactgg agttcagacg tgtgctcttc        60
cgatcttctg gactatgt                                                      78
```

METHOD AND KIT FOR CONSTRUCTING A SIMPLIFIED GENOMIC LIBRARY

CROSS-REFERENCE TO RELATED PATENT APPLICATIONS

The present application is a National Stage of International Patent Application No: PCT/CN2018/074329, filed on Jan. 26, 2018, which claims the benefit of priority to Chinese Patent Application No. 201611193343.X, filed Dec. 21, 2016, which are incorporated by reference in their entirety herein.

SEQUENCE LISTING

The instant application contains a Sequence Listing which has been submitted electronically in ASCII format and is hereby incorporated by reference in its entirety. Said ASCII copy is named PN108272SDYJS_Sequence_listing.txt and is 6.8 kilobytes in size, and contains a sequence listing identical to the sequence listing filed in the corresponding international application no. PCT/CN2018/074329 filed on Jan. 26, 2018.

TECHNICAL FIELD

The present invention relates to the field of construction of high throughput sequencing library, and in particular to a method and kit for constructing a simplified genomic library.

BACKGROUND

Simplified genomic sequencing is a high-throughput sequencing method that uses enzyme digestion technology, sequence capture chip technology or other experimental means to reduce the complexity of the genome of species, and perform sequence determination for part of the genomes, and in turn a technical means to study various genetic structural variations of the genome. It is a generic term for a series of technologies developed on the basis of next-generation sequencing in recent years. Specifically, it refers to a sequencing method that uses bioinformatic methods to design a marker development scheme, enrich specific length fragments, and then uses high-throughput sequencing methods to obtain massive tag sequences to represent the whole genome information of the target species. These methods can develop thousands of markers in a very short time, and molecular markers are the basis for genetic mapping, correlation analysis, population genetic analysis, and ecological diversity analysis, etc., thus developing scientific research work with the method of simplified genomic sequencing is a popular application of the current next-generation sequencing method. Currently, common methods for simplified genomic sequencing include RAD (Restriction site Associated DNA), GBS (Genotyping By Sequencing), and 2b-RAD, and the like.

The RAD simplified genomic method, i.e. is a sequencing method based on restriction site-related DNA markers. The RAD-seq includes steps of: (A) firstly decomposing the genomic DNA with a restriction enzyme, and ligating the P1 adaptor on the decomposed DNA fragments, wherein the P1 adaptor comprises an amplification primer site, an Illumina sequencing primer site, and different ligated tags; (B) decomposing the DNA fragments attached to the adaptors; (C) ligating the P2 adaptor with the "Y" structure to the interrupted fragments, and only fragments with the RAD tags of the P1 and P2 adaptors are ligated at the same time; and (D) a fragment size of about 200-500 bp can be sequenced on a sequencer. The RAD-seq can be sequenced from one end or simultaneously at both ends. The Illumina platform now has a maximum sequencing output of 150 bp, thus sequencing at both ends can output 300 bp of data (DaveyandBlaxter, 2011).

The GBS simplified genomic method refers to genotyping by sequencing. In 2011, it was proposed by Elshire, R. J. The 2b-RAD simplified genomic method is performed based on the type IIB restriction endonuclease cleavage to generate specific fragments for sequencing. The restriction endonucleases BsaXI and AlfI are used to cleave the target sites at upstream and downstream of the genomic DNA, and the produced fragments are suitable for sequencing on the next-generation sequencing platform (see WangS, 2012 for specific procedures).

The simplified genome constructing and sequencing methods based on the above methods all have the following problems: (1) enzyme digestion is required, the requirements for sample DNAs are high, and the efficiency of constructing the library is low. (2) the target fragments obtained have poor random coverage and poor flexible in the genome due to the limitation of the restriction sites, and the disadvantage is that only short restricted fragments can be collected, and the restricted fragments are less; if the target fragments needs to be changed, an appropriate enzyme is needed to be reselected, therefore the target fragments are strictly limited by the cleavage sequence of the endonuclease. (3) It is not possible to construct a library for trace or free samples. (4) Enzyme digestion, interruption, ligation and PCR, etc., are required, and the cycle required for constructing the library is long. (5) There are many reagents required for constructing the library, and the cost is high. (6) The steps of random interruption, fragment selection, and adding Y-type adaptors, etc., are required, which are more complicated.

Therefore, it is still necessary to provide a simplified genomic library method with simple procedure and high efficiency.

SUMMARY

The main object of the present invention is to provide a method and a kit for constructing a simplified genomic library, which can solve the defects that the random fragments can only be obtained by enzymatic cleavage, and the steps are cumbersome and costly in the prior art.

In order to achieve the above object, according to one aspect of the present invention, a method for constructing a simplified genomic library is provided, the method comprises: performing a non-specific amplification on a whole genome with a first pair of primers to obtain random amplified fragments; performing a specific amplification on the random amplified fragments with a second pair of primers to obtain the simplified genomic library.

Further, performing the non-specific amplification on the whole genome by reducing annealing temperature of the first pair of primers to obtain the random amplified fragments.

Further, the first pair of primers sequentially includes a bridging sequence, an optional first tag sequence, and a sequence for non-specific amplification in the 5' to 3' direction.

Further, the sequence for non-specific amplification has one or more degenerate bases, and preferably the number of degenerate bases increases as the number of random amplified fragments to be obtained increases.

Further, the second pair of primers sequentially includes a sequencing adaptor sequence, a sequencing primer sequence, and the bridging sequence in the 5' to 3' direction.

Further, the length of the sequence for non-specific amplification is 4-25 bp; preferably, the length of the first tag sequence is 1-20 bp; further preferably, the length of the bridging sequence is 15-30 bp.

Further, the source of the sequence for non-specific amplification in the first pair of primers is selected from any one of the group consisting of rice, corn, barley, wheat, *arabidopsis*, human and animal.

According to another aspect of the present invention, there is provided a kit for constructing a simplified genomic library, the kit comprises a first pair of primers for a non-specific amplification of a whole genome and a second pair of primers for a specific amplification to the amplified products of the first pair of primers.

Further, the first pair of primers that non-specifically amplifies the whole genome has one or more degenerate bases at the 3' end.

Further, the first pair of primers sequentially includes a bridging sequence, an optional first tag sequence, and a sequence for non-specific amplification in the 5' to 3' direction; preferably, the second pair of primers sequentially includes a sequencing adaptor sequence, a sequencing primer sequence, and a bridging sequence in the 5' to 3' direction; preferably, the length of the sequence for non-specific amplification is 4-25 bp; preferably, the length of the first tag sequence is 1-20 bp; further preferably, the length of the bridging sequence is 15-30 bp; preferably, the source of the sequence for non-specific amplification in the first pair of primers is selected from any one of the group consisting of rice, corn, barley, wheat, *arabidopsis*, human and animal.

According to the third aspect of the present invention, a method of constructing a simplified genomic library is provided, the method comprises: to amplifying a whole genome with a pair of primers to obtain a simplified genomic library; wherein the primers sequentially include a sequencing adaptor sequence, a sequencing primer sequence, a bridging sequence, an optional first tag sequence, and a sequence for non-specific amplification in the 5' to 3' direction.

Further, the whole genome is amplified by reducing the annealing temperature of the primers to obtain the simplified genomic library.

Further, the sequence for non-specific amplification has degenerate bases, and preferably the number of degenerate bases increases as the number of target fragments to be obtained increases.

Further, the length of the sequence for non-specific amplification is 4-25 bp; preferably, the length of the first tag sequence is 1-20 bp; further preferably, the length of the bridging sequence is 15-30 bp.

According to the fourth aspect of the present invention, a kit of constructing a simplified genomic library is provided, the kit comprises a pair of primers to amplify a whole genome, the primers sequentially include a sequencing adaptor sequence, a sequencing primer sequence, a bridging sequence, an optional first tag sequence, and a sequence for non-specific amplification in the 5' to 3' direction.

Further, the sequence for non-specific amplification has one or more degenerate bases at the 3' end; preferably, the length of the sequence for non-specific amplification is 4-25 bp; preferably, the length of the first tag sequence is 1-20 bp; further preferably, the length of the bridging sequence is 15-30 bp.

Applying the technical solution of the present invention, utilizing the characteristics of non-specific amplification having randomness in the genome, a first pair of primers is used firstly to perform non-specific amplification on a whole genome level to obtain the random amplified fragments, then a second pair of primers is used to perform specific amplification on the random amplified fragments to obtain a simplified genomic library. The steps of the method are simple, highly flexible, and cost-effective, and the sequencing results are highly accurate.

The method does not require high-quality or high-concentration DNA, and does not require cumbersome enzymatic digestion and library construction steps, but only simple PCR reaction on the sample DNA is required, and the target fragment can be selected arbitrarily.

By simply changing the PCR annealing temperature or primer sequence, the coverage area of the target fragment in the whole genome can be flexibly controlled; the coverage ratio of different target regions can be obtained by adjusting the degree of non-specific amplification under the same data size. The rapid library construction method provided by the present invention is also applicable to the SNP typing, and solves the problems of cumbersome steps and low efficiency in constructing a library in the prior art.

BRIEF DESCRIPTION OF THE DRAWINGS

The accompanying drawings, which form a part of this application, are provided to further understand the present invention, the illustrative embodiments of the present invention and the description thereof are intended to explain the present invention and are not intended to limit thereto. In the drawings.

DETAILED DESCRIPTION OF THE EMBODIMENTS

It should be noted that the embodiments in the present application and the features in the embodiments may be combined with each other without conflict. The present invention will be described in detail below with reference to the embodiments.

Figure 1:
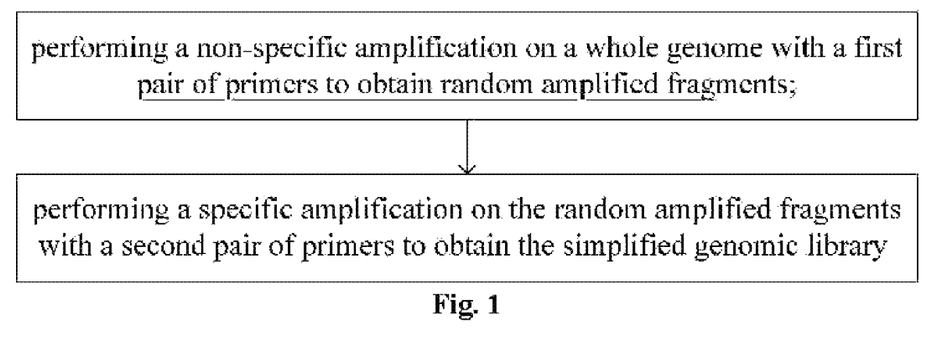
FIG. 1 shows a schematic flow diagram of a method for constructing a simplified genomic library according to a preferred embodiment of the present invention.

As mentioned in background, in the prior art, random fragments can only be obtained by enzymatic cleavage, and there are defects of cumbersome steps and high cost. In order to improve this situation, in a typical embodiment of the present invention, as shown in FIG. 1, a method for constructing a simplified genomic library is provided, the method comprises: performing a non-specific amplification on a whole genome with a first pair of primers to obtain random amplified fragments; using a second pair of primers to perform a specific amplification on the random amplified fragments to obtain a simplified genomic library.

In the prior art, when a primer is used to amplify a target fragment, it is usually sought to increase the specificity of the primer for the amplification of the target fragment, so as to obtain a target fragment of relatively high purity. The inventive idea of this application is precisely by utilizing the characteristics of non-specific amplification having randomness in the genome, a first pair of primers is used firstly to perform non-specific amplification on a whole genome level to obtain the random amplified fragments, then a second pair of primers is used to perform specific amplification on the random amplified fragments to obtain the simplified genomic library. The steps of the method are simple, highly flexible, and cost-effective, and the sequencing results are highly accurate.

The above method does not require high-quality or high-concentration DNA, and does not require cumbersome enzymatic digestion and library construction steps, but only simple PCR reaction on the sample DNA is required, and the target fragment can be selected arbitrarily. By simply changing the PCR annealing temperature or primer sequence, the coverage area of the target fragment in the whole genome can be flexibly controlled; the coverage ratio of different target regions can be obtained by adjusting the degree of non-specific amplification under the same data size. The rapid library construction method provided by the present invention is also applicable to the SNP typing, and solves the problems of cumbersome steps and low efficiency in constructing a library in the prior art.

The biggest innovation of the present invention is that the simplification of the genome is achieved by non-specific amplification of the primers on the genome, thereby obtaining the simplified genomic library only by PCR without the step of enzymatic cleavage. While the specific implementation of performing non-specific amplification on the whole genome by the first pair of primers is not particularly limited, and can be achieved by a method capable of causing non-specific amplification in the prior art. For example, the whole genome can be non-specifically amplified by reducing the annealing temperature of the first pair of primers to obtain random amplified fragments. Non-specific amplification can also be achieved by way of designing degenerate bases, and the number of degenerate bases increases as the number of random amplified fragments to be obtained increases.

The first pair of primers described above are reasonably selected or designed by oneself according to the size of the genome of the studied species and the output data size. In a preferred embodiment of the present invention, the first pair of primers sequentially includes a bridging sequence, an optional first tag sequence, and a sequence for non-specific amplification in the 5' to 3' direction. The bridging sequence referred to herein refers to a sequence overlapping with the second pair of primers, and the specific amplification of the random amplified fragment is achieved by the specific binding of the second pair of primers to the bridging sequence of the first pair of primers, thereby obtaining the simplified genomic library.

Accordingly, any primers capable of specifically binding to the first pair of primers and specifically amplifying to obtain a sequencing library that can be applied to the sequencing platform for high-throughput sequencing can be used. In a preferred embodiment of the present invention, the second pair of primers described above sequentially includes a sequencing adaptor sequence, a sequencing primer sequence, and a bridging sequence in the 5' to 3' direction.

The length of the sequence for non-specific amplification in the first pair of primers can be appropriately selected according to actual needs. Similarly, the length of the first tag sequence and the bridging sequence can also be selected as required. Preferably, the length of the sequence for non-specific amplification is 4-25 bp; more preferably, the length of the first tag sequence is 1-20 bp; further preferably, the length of the bridging sequence is 15-30 bp.

Depending on the studied species, the source of the sequence for non-specific amplification in the first pair of primers includes but not limited to any one of rice, corn, barley, wheat, *arabidopsis*, human and animal.

In another typical embodiment of the present invention, there is also provided a kit for constructing a simplified genomic library, the kit comprises a first pair of primers for non-specific amplification of a whole genome and a second pair of primers for specific amplification to the amplified products of the first pair of primers. Using such primers containing non-specific amplification and primers for specifically amplifying non-specifically amplified products, the simplified genome can be obtained by simply performing the two-step PCR without enzymatic cleavage, which not only simplifies the library construction process, but also reduces the cost of constructing a library.

The first pair of primers in the above kit may be any primer capable of performing non-specific amplification on the target genome. Preferably, the first pair of primers that non-specifically amplifies the whole genome has one or more degenerate bases at the 3' end. The greater the number of degenerate bases, the greater the number of the available random amplified fragments is. The exact number of degenerate bases can be reasonably selected according to actual requirements.

The sequence composition of the first pair of primers described above is selected as long as it can perform non-specific amplification and is capable of performing the second specific amplification. In order to mark the source of the different amplified target fragments, in a preferred embodiment, the first pair of primers described above sequentially includes a bridging sequence, an optional first tag sequence, and a sequence for non-specific amplification in the 5' to 3' direction.

Similarly, in the above kit, the length of the non-specific amplification sequence in the first pair of primers can be appropriately selected according to actual needs. Similarly, the length of the first tag sequence and the bridging sequence can also be selected as required. Preferably, the length of the sequence for non-specific amplification is 4-25 bp; more preferably, the length of the first tag sequence is 1-20 bp; further preferably, the length of the bridging sequence is 15-30 bp.

Depending on the studied species, the source of the first pair of primers described above includes but not limited to any one of rice, corn, barley, wheat, *arabidopsis*, human and animal.

It should be noted that, in the method of the present invention, the amplification product obtained after the first non-specific amplification and/or the second specific amplification can also be subjected to a purification step to remove the impurities such as enzyme proteins in the PCR system and primer dimers, so that the non-specific amplified fragments in the obtained simplified genomic library are more pure. The specific purification method may be purified by electrophoresis gel-gel cutting or magnetic beads.

In the present invention, in order to achieve the object of non-specific amplification on the whole genome, on the one hand, non-specific amplification can be achieved by increasing the degeneracy or diversity of the sequences for non-specific amplification; on the other hand, by reducing the annealing temperature of the PCR reaction, the non-specific binding of the sequence for non-specific amplification of the primer at 3' end to the template is achieved, so that the non-specific amplification can be achieved. The lower the annealing temperature is, the greater the number of non-specific amplified fragments is. Simplified genomic information with different coverage can be obtained by setting different annealing temperatures.

According to the third aspect of the present invention, a method for constructing a simplified genomic library is provided, the method comprises: using a pair of primers to amplify a whole genome to obtain a simplified genomic library; wherein, the primers sequentially comprise a sequencing adaptor sequence, a sequencing primer sequence, a bridging sequence, an optional first tag sequence, and a sequence for non-specific amplification in the 5' to 3' direction.

The method for constructing the simplified genomic library is one-step amplification method, which is common with the two-step amplification method described above in that it is a non-specific amplification when the primers are used to amplify the whole genome. The only difference is that the specific amplified primer of the second step described above and the primer of the non-specific amplification step are directly combined to be one primer, so that the random non-specific amplification of the primer on the whole genome is not affected, and the specific amplification of the non-specifically amplified fragments is realized, thereby further simplifying the process of whole genome library construction and improving the efficiency of the library construction.

Similarly, when the whole genome is amplified by only a pair of primers, the whole genome can be amplified by both reducing the annealing temperature of the primers and using a degenerate base to obtain a simplified genomic library. The two implementations can be reasonably selected or comprehensively optimized according to actual conditions. In a preferred embodiment, the whole genome is amplified by reducing the annealing temperature of the primers to obtain a simplified genomic library. In another preferred embodiment, the sequence for non-specific amplification described above has degenerate bases, and preferably the number of degenerate bases increases as the number of target fragments to be obtained increases.

The length of the specific sequence for non-specific amplification, the first tag sequence and the bridging sequence can be appropriately adjusted based on the length of the sequences in prior art. In a preferred embodiment, the length of the sequence for non-specific amplification described above is 4-25 bp; more preferably, the length of the first tag sequence is 1-20 bp; further preferably, the length of the bridging sequence is 15-30 bp.

According to the fourth aspect of the present invention, a kit for constructing a simplified genomic library is provided, the kit comprises a pair of primers to amplify a whole genome, the primers sequentially comprise a sequencing adaptor sequence, a sequencing primer sequence, a bridging sequence, an optional first tag sequence, and a sequence for non-specific amplification in the 5' to 3' direction. The kit can both realize the random amplification of DNA fragments on the whole genome, and has the advantage of simple library construction process, and only a one-step amplification step is required to obtain the simplified genomic library.

In the above kit, the length of the specific sequence for non-specific amplification, the first tag sequence and the bridging sequence can be appropriately adjusted based on the length of the sequences in prior art. In a preferred embodiment, the length of the sequence for non-specific amplification described above is 4-25 bp; more preferably, the length of the first tag sequence is 1-20 bp; further preferably, the length of the bridging sequence is 15-30 bp.

In order to make the objects, technical solutions and advantages of the present invention more clear, the various embodiments of the present invention will be described in detail below with reference to specific examples.

Figure 2:
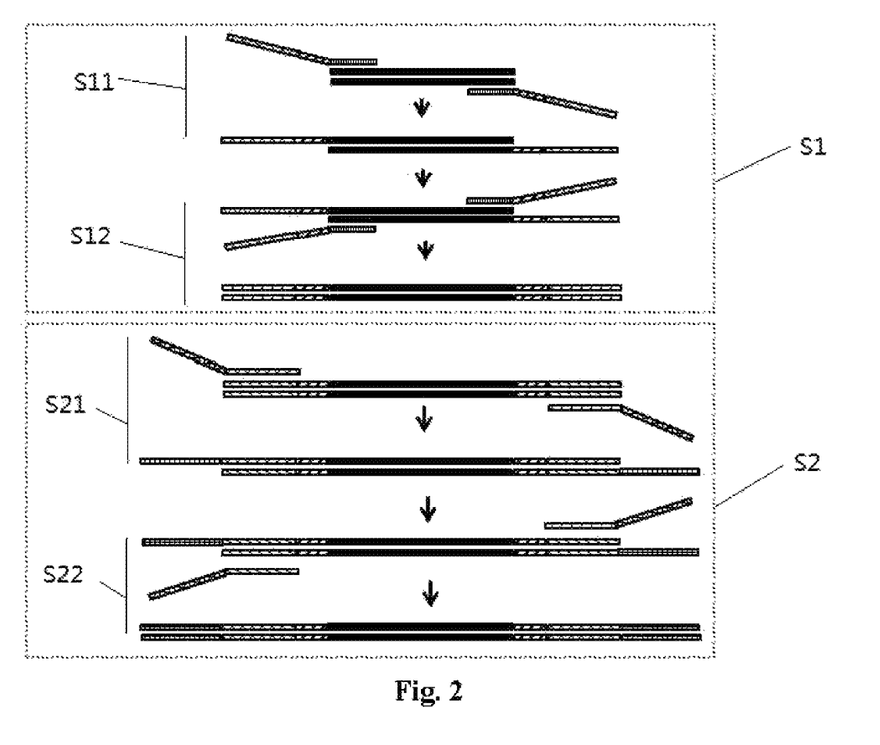
FIG. 2 shows a detailed schematic flow diagram of two amplifications in the method for constructing a simplified genomic library according to a preferred embodiment of the present invention.

Referring to FIG. 2, FIG. 2 is a detailed schematic flow diagram of an embodiment of a method for construction of a simplified genome sequencing library of the present invention, comprising:

Step S1: performing non-specific PCR reaction on the sample DNA using the first pair of primers. Wherein, the sequences of the first pair of primers sequentially comprises a bridging sequence, a tag sequence and a sequence for non-specific amplification from the 5' end to the 3' end; wherein the length of the sequence for non-specific amplification is not limited, generally set to 4-25 bp; the length of the tag sequence is not limited, generally set to 1-20 bp; and the length of the bridging sequence is not limited, generally set to 15-30 bp. When PCR amplification is performed, changing the annealing temperature of the PCR reaction, controlling the number of the 3' end of the primer sequence for non-specific amplification that matches with the template DNA, or increasing the degeneracy or diversity of the sequence for non-specific amplification, thereby controlling the distribution of amplified fragments in the whole genome to obtain a simplified genomic information with various degrees of coverage.

If multi-sample mixing sequencing is required, different combinations of tag sequences can be used in PCR, so that different samples can be easily distinguished subsequently.

Specific steps are as follows:

Step S11, annealing and extending the genomic sequences that the first upstream primer and the first downstream primer respectively non-specifically bind to in order to obtain an extended fragment with a primer sequence at one end;

Step S12, using the extended fragment with a primer sequence at one end as a template, and re-amplifying with the first upstream primer and the first downstream primer to obtain random amplified fragments with primer sequences at both ends.

Step S2: Performing the second round of PCR with the first round of products as templates.

The second round of primers contains the same bridging sequence as the first pair of primers, so that the first round of non-specific amplification product can be added with sequencing probe binding sequences and sequencing adaptor sequences by the second round of PCR reaction (also including the step of ligating the primer at one end of S21 and the step of ligating the primer at both ends of S22).

It should be noted that, for the sake of convenience, the two pairs of primers in the present invention may also be integrated into one pair of primers, that is, it sequentially comprises from the 5' end to the 3' end a sequencing probe binding sequence (or a adaptor sequence) sequencing primer sequence, a tag sequence and a sequence for non-specific amplifications, so that only one round of non-specific PCR is required to complete the library construction, but finally the library contains a part of single primer amplified fragments. Which method is used can be selected according to actual needs.

Step S3: separating and purifying the second round of PCR products, that is, the obtained simplified genomic library.

The second round of PCR products contains other impurity components of different size of fragments, and after isolation and purification, a PCR product with sequencing primers is obtained.

Step S4: Gene sequencing the second DNA products, and analyzing the sequencing results to obtain the sequencing result of each DNA sequence.

The second DNA product can be sequenced using the sequencing techniques in prior art, such as Illumina's sequencer, and the sequencing results can be analyzed to obtain sequencing results for each DNA sequence.

Since each DNA sequence has a tag sequence, the same tag sequence is the same DNA sequence. After obtaining all the DNA sequencing results, sorting is performed according to the tag sequence, all the DNA sequencing results belonging to the same DNA sequence can be obtained.

Advantageous effects of the present application will be further described below in conjunction with specific examples. It should be noted that in the following examples, the reagents used were all from Toyobo Co., Ltd. unless otherwise specified.

Example 1

I. Extraction of Genomic DNA to be Tested

The genomic DNA of the leaves of Nipponbare individual rice was extracted and used as a library construction object for the present example. The extraction operation is briefly described as follows:

1.1 100 mg of fresh leaf tissue was selected, and liquid nitrogen was added and fully ground;
1.2 DNA was extracted with the Tiangen plant genomic DNA extraction kit or CTAB method;
1.3 The extracted DNA was subjected to quality control.

II. PCR Amplification to Enrich the Target Regions(PCR-1)

1. Primer Design

1) The unique bridging primers, tag sequences and non-specific sequences were designed at 5'→3' end of the forward primers (1P-1F, 1P-2F, 1P-3F, 1P-4F) and reverse primers (1P-1R, 1P-2R, 1P-3R, 1P-4R);

2) Specific Primer Sequence Information was Shown in Table 2.

Table 2:

TABLE 2

| Primer name | SEQ ID No: | sequence |
|---|---|---|
| 1-1F | 3 | GACGCTCTTCCGATCTCAGTAGGTTCTGGACTAACG |
| 1-2F | 4 | GACGCTCTTCCGATCTCAGTAGGTTCTGGACTAACA |
| 1-3F | 5 | GACGCTCTTCCGATCTCAGTAGGTTCTGGACTAACT |

TABLE 2-continued

| Primer name | SEQ ID No: | sequence |
|---|---|---|
| 1-4F | 6 | GACGCTCTTCCGATCTCAGTAGGTTCTGGACTAAGG |
| 1-1R | 7 | GACGTGTGCTCTTCCGATCTTCTGGACTATGC |
| 1-2R | 8 | GACGTGTGCTCTTCCGATCTTCTGGACTATGG |
| 1-3R | 9 | GACGTGTGCTCTTCCGATCTTCTGGACTATGA |
| 1-4R | 10 | GACGTGTGCTCTTCCGATCTTCTGGACTATGT |

2. PCR Amplification

1) Different primer pairs were added to the sample genomic DNAs for PCR amplification, respectively, and a negative control CK was added;

2) PCR was performed in KODFX 20 μL reaction system;

| 2 × KODFX Buffer | 10 μL |
|---|---|
| 2 mM dNTPs | 4 μL |
| FP (10 uM) | 0.6 μL |
| RP (10 uM) | 0.6 μL |
| KODFX Polymerase | 0.4 μL |
| DNA template | 0.4 μL |
| ddH$_2$O | 4 μL |

3) PCR instrument: LY96G/Y, multifunctional PCR gene amplification instrument.

The PCR reaction procedure was as follows: (wherein the symbol×indicates cycling, and 2×indicates that two cycles were performed):
  a. 1×(94° C., 2 min)
  b. 2×(98° C., 10 s; 25° C., 2 min; jump to 68° C. (at a temperature rise rate of 0.8° C./s))
  c. 1×(68° C., 2 min)
  d. 35×(98° C., 10 s; 58° C., 30 s; 68° C., 1 min)
  e. 1×(68° C., 5 min)

Figure 3:
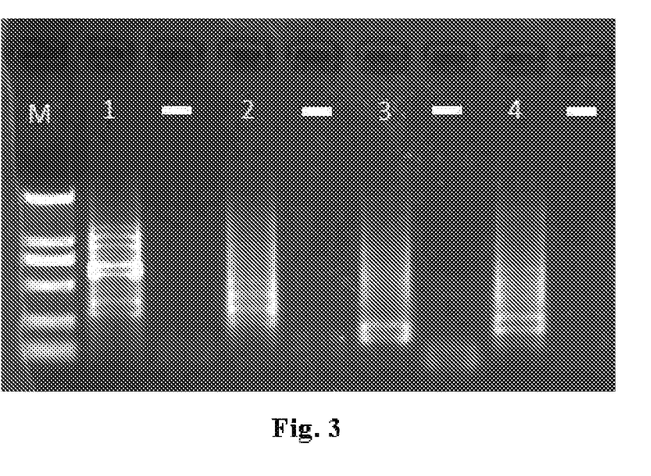
FIG. 3 is a diagram showing an electrophoresis result of random amplified fragments obtained after non-specific amplification according to Example 1 of the present invention.

4) The PCR product was detected by 2% gel electrophoresis, and DL2000 was used as a molecular marker, and 3 μL was loaded for detection. The electrophoresis pattern of some samples was shown in FIG. 3. In FIG. 3, 1 represents an amplification product of 1F+1R; 2 represents an amplification product of 2F+2R; 3 represents an amplification product of 3F+3R; 4 represents an amplification product of 4F+4R; "-" represents a control, the DNA sample was replaced with ultrapure water.

III. Introduction of Sequencing Adaptor (PCR-2) by PCR Amplification

1. Primer Design

1) The amplified region was the sequence between the bridging primers in the first PCR product, thus the designed primer had a sequence at the 3' end that was complementary to the bridging sequence in the first PCR product.

2) The forward primer SEQ ID No: 11 had a P5 sequence at the 5' end, and the reverse primer SEQ ID No: 12 had an Index sequence and a P7 sequence at the 5' end.

3) The primer specific information was as follows:

SEQ ID No: 11:
AATGATACGGCGACCACCGAGATCTACACTCTTTCCCTACACGACGCTC
TTCCGATCTCAGT;

-continued

SEQ ID No: 12:
CAAGCAGAAGACGGCATACGAGATCGCTGATCGTGACTGGAGTTCAGAC
GTGTGCTCTTCCGATCT;

3. PCR Amplification (PCR-2)
1) The first PCR product diluted 100-fold was used as a DNA template for PCR amplification.
2) PCR was performed in KODFX 20 µL reaction system:

| | |
|---|---|
| 2 × KODFX Buffer | 10 µL |
| 2 mM dNTPs | 4 µL |
| FP (10 uM) | 0.6 µL |
| RP (10 uM) | 0.6 µL |
| KODFX Polymerase | 0.4 µL |
| DNA template | 0.4 µL |
| ddH$_2$O | 4 µL |

Figure 4:
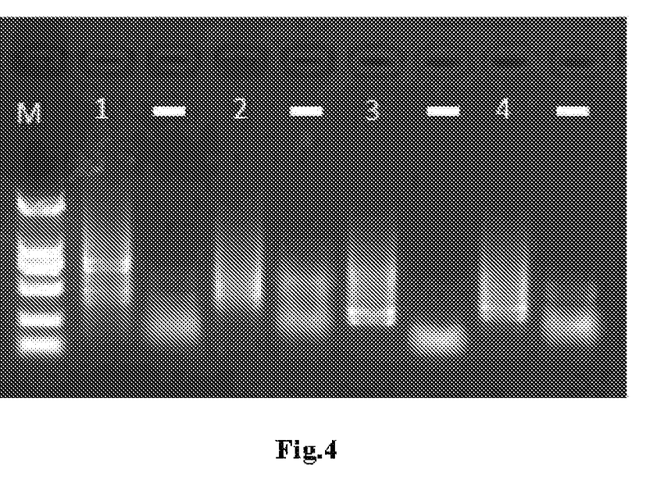
FIG. 4 is a diagram showing an electrophoresis result of amplified products obtained after specific amplification according to Example 1 of the present invention.

3) PCR instrument: LY96G/Y, multifunctional PCR gene amplification instrument
The PCR reaction procedure was as follows:
a. 1×(94° C., 2 min)
b. 2×(98° C., 10 s; 58° C., 30 s)
c. 1×(68° C., 2 min)
d. 35×(98° C., 10 s; 68° C., 90 s)
e. 1×(18° C., 2 min)
4) The PCR product was detected by 2% gel electrophoresis, and DL2000 was used as a molecular marker, and 2 µL was loaded for detection. The electrophoresis pattern was shown in FIG. 4. In FIG. 4, 1 represents an amplification product of 1F+1R; 2 represents an amplification product of 2F+2R; 3 represents an amplification product of 3F+3R; 4 represents an amplification product of 4F+4R; "-" represents a control, the DNA sample was replaced with ultrapure water.

IV. Library Inspection and Uploading.
1. The PCR product obtained in the step 3 was diluted to 1 ng/µL, and 1 µL was taken for detection by Agilent 2100 (Agilent, USA), and another 1 µL was taken for qPCR (Biorad) detection, and the concentration of the uploading was determined based on the detection result.
2. Based on the concentration obtained in the last step, the library was diluted to the uploading concentration and sequenced on Illumina's Hiseq2000 sequencing platform.

V. Quality Control of Uploading, Sequencing and Bioinformatics Analysis of Sequencing Data
1. Sequencing
The DNA library obtained by the above-described two-step method of the present invention was sequenced by Illumina's Hiseq sequencing platform, and each library was sequenced for 1 Gb of data size.
2. Data Analysis
Four rice resequencing samples were subjected to library construction and sequencing by the above methods.
The results were analyzed as follows:
Q20, Q30: Q20, Q30 of PoolRice was reached 98% or more, and for re-sequencing projects: Q20 was required to be not less than 90%; Q30 was not less than 85%, even in the de novo sequencing (De novo) project, Q20 was required to be not less than 95%; Q30 was required to be not less than 90%, thus the sequencing quality was good.

Adapter contamination rate: The primer adapter rate of the mixed library construction was 0.02%, 0.03%, and 0.02%, respectively. The primer adapter rate less than 5% was considered to be normal, thus the primer adapter rate was normal.

Duplication: The duplication of this mixed library construction was 85%, 82.2%, and 82.5%. The duplication of mixed library construction was generally high. The duplication of this mixed library construction was within the allowable range.

Figure 5:
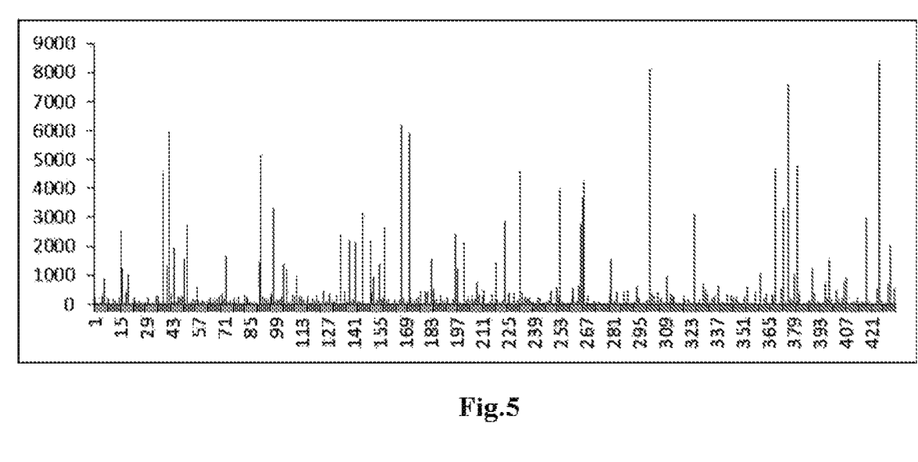
FIG. 5 is a diagram showing the distribution of random amplified fragments on chromosome 1 in the sequencing results of the simplified genomic library constructed according to Example 1 of the present invention.

In summary, the library construction was qualified and the sequencing quality was good. Moreover, reference genome alignment analysis was performed on valid sequencing data (Clean data) to detect the distribution of random fragments amplified by the method of the present example on the genome, and it was found that the distribution on the genome was uniform and met the requirements of the simplified genomic library. Wherein, FIG. 5 shows the distribution of the random amplified sequence on chromosome 1, and the abscissa indicates the distance on the genome, with 100 KB as the statistical window and the ordinate indicates the number of non-specific amplified fragments. It can be seen that the distribution on chromosome 1 is relatively uniform.

Example 2

The only difference between the procedures of Example 2 and Example 1 was the procedure for the first round of PCR reactions. Specific procedure was as follows:
a. 1×(94° C., 2 min)
b. 2×(98° C., 10 s; 15° C., 2 min; jump to 68° C. (at a temperature rise rate of 0.8° C./s))
c. 1×(68° C., 2 min)
d. 35×(98° C., 10 s; 58° C., 30 s; 68° C., 1 min)
e. 1×(68° C., 5 min)
The DNA library obtained by the above-described two-step library construction method was sequenced by Illumina's Hiseq sequencing platform, and each library was sequenced for 1 Gb of data size. The data analysis results were as follows:
Q20, Q30: Q20, Q30 of Pool Rice was reached 94% or more, thus the sequencing quality was good.

Example 3

I. DNA extraction step (the same as in Example 1)
II. PCR amplification to enrich the target regions(PCR-1):
1. The first round of PCR reaction was carried out with the primers shown in Table 3, the reaction system, and the PCR reaction procedure were the same as in Example 1.

TABLE 3

| Primer name | SEQ ID No: | Sequence |
|---|---|---|
| 2-1F | 13 | CGACGCTCTTCCGATCTTGACGCCATGTCTGGACTAACA |
| 2-2F | 14 | CGACGCTCTTCCGATCTTGACGCCACATCTGGACTAACA |

TABLE 3-continued

| Primer name | SEQ ID No: | Sequence |
|---|---|---|
| 2-3F | 15 | CGACGCTCTTCCGATCTTGACGCCACTTCTGGACTAACA |
| 2-4F | 16 | CGACGCTCTTCCGATCTTGACGCCACCTCTGGACTAACA |
| 2-5F | 17 | CGACGCTCTTCCGATCTTGACGCCAGGTCTGGACTAACA |
| 2-1R | 18 | GTGTGCTCTTCCGATCTCAGTCCCATCTCTGGACTATGG |
| 2-2R | 19 | GTGTGCTCTTCCGATCTCAGTCCCATGTCTGGACTATGG |
| 2-3R | 20 | GTGTGCTCTTCCGATCTCAGTCCCACATCTGGACTATGG |
| 2-4R | 21 | GTGTGCTCTTCCGATCTCAGTCCCACTTCTGGACTATGG |
| 2-5R | 22 | GTGTGCTCTTCCGATCTCAGTCCCACCTCTGGACTATGG |

1) The unique bridging primers, tag sequences and non-specific sequences were designed at 5' to 3' end of the forward primers (2-1F, 2-2F, 2-3F, 2-4F, 2-5F) and reverse primers (2-1R, 2-2R, 2-3R, 2-4R, 2-5R);

III. The Second Round of PCR 6 of the first round of PCR products were mixed in equal amounts into one mixed sample, and the mixed sample was subjected to a second round of PCR (the conditions of PCR reaction were the same as in Example 1).

IV. Library Inspection and Uploading (Consistent with Example 1).

The analysis results of the sequencing data were as follows:

Q20, Q30: Q20, Q30 of PoolRice was reached 93% or more, thus the sequencing quality was good.

The 1Gb data obtained by sequencing the library was analyzed, and the sequencing data results with equal-proportion of the mixed 6 materials were obtained with the barcode added at both ends.

In summary, the library construction was qualified and the sequencing quality was good.

Example 4

The difference between the operating procedure in Example 4 and that of Example 1 is that the primers of the first and second round of PCR were combined, and only one PCR was performed. The specific sequences are as follows:

TABLE 4

| Primer name | SEQ ID No: | Sequence |
|---|---|---|
| 3-1F | 25 | AATGATACGGCGACCACCGAGATCTACACTCTTTCCCTACACGACGCTCTTCCGATCTCAGTAGGTTCTGGACTAACG |
| 3-2F | 26 | AATGATACGGCGACCACCGAGATCTACACTCTTTCCCTACACGACGCTCTTCCGATCTCAGTAGGTTCTGGACTAACA |
| 3-3F | 27 | AATGATACGGCGACCACCGAGATCTACACTCTTTCCCTACACGACGCTCTTCCGATCTCAGTAGGTTCTGGACTAACT |
| 3-4F | 28 | AATGATACGGCGACCACCGAGATCTACACTCTTTCCCTACACGACGCTCTTCCGATCTCAGTAGGTTCTGGACTAAGG |
| 3-1R | 29 | CAAGCAGAAGACGGCATACGAGATCGCTGATCGTGACTGGAGTTCAGACGTGTGCTCTTCCGATCTTCTGGACTATGC |
| 3-2R | 30 | CAAGCAGAAGACGGCATACGAGATCGCTGATCGTGACTGGAGTTCAGACGTGTGCTCTTCCGATCTTCTGGACTATGG |
| 3-3R | 31 | CAAGCAGAAGACGGCATACGAGATCGCTGATCGTGACTGGAGTTCAGACGTGTGCTCTTCCGATCTTCTGGACTATGA |
| 3-4R | 32 | CAAGCAGAAGACGGCATACGAGATCGCTGATCGTGACTGGAGTTCAGACGTGTGCTCTTCCGATCTTCTGGACTATGT |

Figure 6:
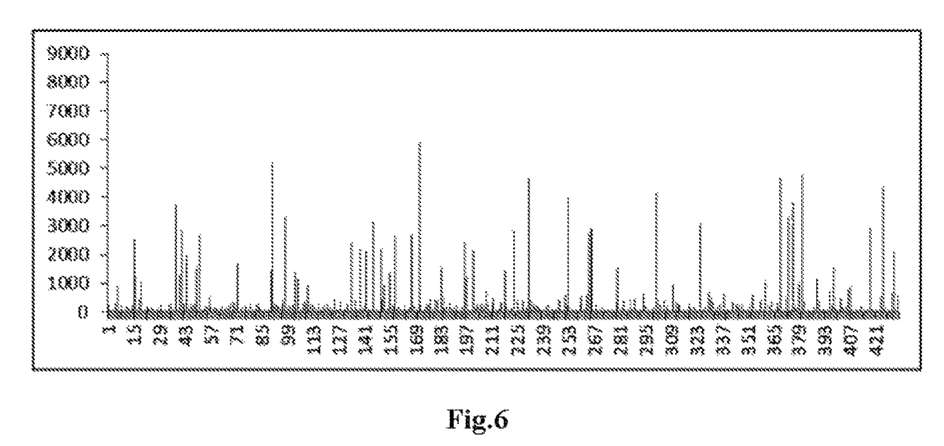
FIG. 6 is a diagram showing the distribution of random amplified fragments on chromosome 1 in the sequencing results of the simplified genomic library constructed according to the one step amplification method in Example 4 of the present invention.

The DNA library obtained by the above-described one-step library construction method was sequenced by Illumina's Hiseq sequencing platform, and each library was measured for 1.2 Gb of data size. The data analysis results were as follows:

Q20, Q30: Q20, Q30 of Pool Rice was reached 96% or more, thus the sequencing quality was good. Moreover, reference genome alignment analysis was performed on valid sequencing data (Clean data) to detect the distribution of random fragments amplified by the method of the present example on the genome. The results were shown in FIG. 6, the abscissa indicates the distance on the genome, with 100 KB as the statistical window and the ordinate indicates the number of non-specific amplified fragments. It can be seen from the FIG. 6 that the distribution of the random amplified fragments in the simplified genomic libraries on chromosome 1 is relatively uniform.

In addition, it should be noted that the library construction method of the present invention comprises two steps of PCR non-specific amplification and enrichment of the target region and PCR amplification and introduction of sequencing adaptor, and the specific operation mode of the two steps is not limited to the method shown in the above embodiment. Other methods may be used, and the overall function and process are unchanged. For example, other methods may be employed in the PCR non-specific amplification enrichment target region, and the methods are not limited to direct non-specific amplification enrichment to the target DNA region, such as non-specific amplification enrichment of RNA by RT-PCR; in the process of the PCR amplification and introduction of sequencing adaptor, the purification method of the PCR product can also be replaced by other methods, such as recycling the target band by gel cutting. Sequencing can be carried out as the sequencing methods in prior art, or by constructing high-throughput sequencing pathways, etc.

It can be seen that the above-described embodiments of the present invention achieve the following technical effects:

(1) Simple and convenient: the present invention realizes non-specific amplification of whole genome fragments by simple PCR reaction, and requires only one pair of primers for one PCR reaction, and obtains information of simplified genome. The whole library construction process is simple and easy to operate.

(2) High flexibility: the sequence, number or annealing temperature of primer can be randomly changed according to the experimental requirements to change the distribution of amplified fragments in the whole genome, and personalized development solutions can be developed and designed with the information of known genomes and the number of non-specific matches.

(3) Low cost: only simple PCR amplification is required. Compared with the prior art, the cost of the kit is eliminated, the cost of amplicon library construction and sequencing is greatly reduced, and the efficiency is improved; and the mutations that may be introduced due to the cumbersome steps in the conventional library construction are avoided, the sequencing quality is not affected by the two-step method compared with the conventional library construction, and the sequencing quality is more accurate.

(4) Short cycle: only a simple PCR reaction can be used to complete the library construction, and the time is less than 5 hours, which greatly shortens the cycle of the library construction.

(5) High sensitivity: there is no special requirement for sample amount and concentration. Library construction and sequencing analysis can be performed for free DNA, degraded fragmented DNA, trace DNA, single-cell DNA, etc., and even crude samples, as long as they can be subjected to the PCR reaction.

The above description is only the preferred embodiment of the present invention, and is not intended to limit the present invention, and various modifications and changes can be made to the present invention for those skilled in the art. Any modifications, equivalent substitutions, improvements, etc. made within the spirit and scopes of the present invention are intended to be included within the protection scopes of the present invention.

What is claimed is:

1. A method for constructing a simplified genomic library, wherein the method consists of:
performing a non-specific PCR amplification on a whole genome with one first pair of primers annealing at 25° C. to obtain random amplified fragments;
performing a specific PCR amplification on the random amplified fragments with one second pair of primers to obtain the simplified genomic library;
wherein each primer of the first pair of primers sequentially comprises a bridging sequence, a first tag sequence, and a sequence for non-specific amplification in the 5' to 3' direction, wherein the first pair of primers is
SEQ ID NO:4 and SEQ ID NO:8;
wherein each primer of the second pair of primers sequentially comprises a sequencing adaptor sequence, a sequencing primer sequence, and the bridging sequence in the 5' to 3' direction.

2. A kit for constructing a simplified genomic library, wherein the kit consists of one first pair of primers for a non-specific PCR amplification of a whole genome and one second pair of primers for a specific PCR amplification of the amplified products of the first pair of primers, wherein each primer of the first pair of primers sequentially comprises a bridging sequence, a first tag sequence, and a sequence for non-specific PCR amplification in the 5' to 3' direction, wherein the first pair of primers is
SEQ ID NO:4 and SEQ ID NO:8;
wherein each primer of the second pair of primers sequentially comprises a sequencing adaptor sequence, a sequencing primer sequence, and the bridging sequence in the 5' to 3' direction.

* * * * *